(12) United States Patent
Trubiano et al.

(10) Patent No.: US 8,252,322 B2
(45) Date of Patent: Aug. 28, 2012

(54) DELIVERY SYSTEM WITH INCREASED BIOAVAILABILITY

(75) Inventors: Paolo C. Trubiano, Somerville, NJ (US); Afaf Karras, East Brunswick, NJ (US)

(73) Assignee: Corn Products Development, Inc., Westchester, IL (US)

( * ) Notice: Subject to any disclaimer, the term of this patent is extended or adjusted under 35 U.S.C. 154(b) by 1554 days.

(21) Appl. No.: 10/453,011

(22) Filed: Jun. 3, 2003

(65) Prior Publication Data
US 2004/0247658 A1 Dec. 9, 2004

(51) Int. Cl.
| | |
|---|---|
| *A61K 9/20* | (2006.01) |
| *A61K 9/46* | (2006.01) |
| *A61K 9/00* | (2006.01) |
| *A61K 38/43* | (2006.01) |
| *A61K 31/715* | (2006.01) |
| *A61K 31/66* | (2006.01) |
| *A61K 31/56* | (2006.01) |
| *A61K 31/35* | (2006.01) |
| *A61K 31/34* | (2006.01) |
| *A61K 31/20* | (2006.01) |
| *A61K 31/07* | (2006.01) |
| *A61K 31/01* | (2006.01) |
| *A61K 9/14* | (2006.01) |
| *A01N 25/00* | (2006.01) |
| *A01N 45/00* | (2006.01) |

(52) U.S. Cl. ........ 424/450; 424/400; 424/405; 424/408; 424/465; 424/466; 424/484; 424/488; 424/499; 424/94.1; 514/54; 514/114; 514/168; 514/169; 514/456; 514/458; 514/475; 514/558; 514/560; 514/725; 514/762; 536/105; 536/106; 536/102

(58) Field of Classification Search .................. 424/450, 424/400, 465, 466, 484, 488, 499; 536/102, 536/105, 106
See application file for complete search history.

(56) References Cited

U.S. PATENT DOCUMENTS

| | | | |
|---|---|---|---|
| 4,636,381 A * | 1/1987 | Takada et al. ................. | 424/450 |
| 4,859,377 A * | 8/1989 | Shasha et al. .................. | 264/4.1 |
| 4,977,252 A | 12/1990 | Chiu | |
| 4,985,082 A * | 1/1991 | Whistler ......................... | 127/33 |
| 5,185,176 A | 2/1993 | Chiu | |
| 5,492,648 A | 2/1996 | Lau et al. | |
| 5,783,211 A | 7/1998 | Manzo et al. | |
| 6,045,823 A | 4/2000 | Vollhardt et al. | |
| 6,086,917 A * | 7/2000 | Trubiano et al. ............. | 424/465 |
| 6,387,398 B1 | 5/2002 | Vollhardt et al. | |
| 6,403,116 B1 | 6/2002 | Anderson et al. | |

FOREIGN PATENT DOCUMENTS

| | | |
|---|---|---|
| EP | 0 913 406 | 5/1999 |
| EP | 0 922 449 | 6/1999 |
| WO | WO 89/04842 A | 6/1989 |
| WO | WO 97/22333 | 6/1997 |

* cited by examiner

*Primary Examiner* — John Pak
*Assistant Examiner* — Nathan W Schlientz
(74) *Attorney, Agent, or Firm* — Thomas C. McKenzie; Karen Kaiser

(57) ABSTRACT

The present invention is directed to a dry composition which allows delivery of active agents with good bioavailability. These compositions are prepared by emulsifying the active agent using liposome technology known in the art and then encapsulating with a modified starch. The modified starch is prepared by enzymatic hydrolysis of starch after the preparation of a starch derivative containing a hydrophobic group or both a hydrophobic and a hydrophilic group. The resultant composition is a dry powder with excellent bioavailability. Further, the composition has good load levels and stability.

18 Claims, No Drawings

DELIVERY SYSTEM WITH INCREASED BIOAVAILABILITY

BACKGROUND OF THE INVENTION

The present invention relates to a delivery system with increased bioavailability. Many active agents are substantially biologically inactive in their dry form. One way of delivering biologically active agents of this type is in the form of a liquid, such as through the use of liposomes.

However, consumers typically prefer to take such active agents in the form of a tablet or other solid dosage form. This obstacle has been overcome by using conventional forms of encapsulation. A variety of chemical compositions are conventionally used as encapsulating agents to deliver dry material in, inter alia, the food, cosmetic, paint, pharmaceutical, personal care, household, and polymer industries. Typical compositions which conventionally function as encapsulating agents include gum arabic, dextrins, starches, arabinogalactan, gum acacia, casein, gelatin, carboxymethyl cellulose, tragacanth, karaya, sodium alginate, tannin, and celluloses. While these compositions are successful in transforming the active agent into a dry powder, they do so as a substantial cost to the bioavailability.

Surprisingly, it has now been discovered that the present invention which uses a modified starch, prepared by enzymatically converting a starch after the preparation of a starch derivative containing a hydrophobic group or a hydrophobic and a hydrophilic group, as an encapsulating agent consistently allows for high bioavailability.

SUMMARY OF THE INVENTION

The present invention is directed to a dry composition which allows delivery of active agents with good bioavailability. These compositions are prepared by emulsifying the active agent using liposome technology known in the art and then encapsulating with a modified starch. The modified starch is prepared by enzymatic hydrolysis of starch after the preparation of a starch derivative containing a hydrophobic group or both a hydrophobic and a hydrophilic group. The resultant composition is a dry powder with excellent bioavailability. Further, the composition has good load levels and stability.

DETAILED DESCRIPTION OF THE INVENTION

The present invention is directed to a dry composition which allows delivery of active agents with good bioavailability. These compositions are prepared by emulsifying the active agent using liposome technology known in the art and then encapsulating with a modified starch. The preparation of liquid liposomal active ingredients is typically covered in the patent literature, such as U.S. Pat. Nos. 5,783,211 and 5,492,648. The modified starch is prepared by enzymatic hydrolysis of starch after the preparation of a starch derivative containing a hydrophobic group or both a hydrophobic and a hydrophilic group. The resultant composition is a dry powder with excellent bioavailability, good load levels and stability. The composition also has good load levels and retention of the active ingredient, low surface oil exposure, and excellent oxidation resistance. Further, such encapsulating agents can be processed at higher solids than many conventional encapsulating agents.

Any active agent with low bioavailability in its dry form is particularly suitable for encapsulation by the present invention, particularly aqueous insoluble dietary and nutritional supplements such as vitamins, fatty acids, and antioxidants. Of particular importance are coenzyme Q10, conjugated linoleic acid, omega 3/6 fatty acids (marine oils), saw palmetto, phosphatidylcholine (PC), phosphatidylserine (PS), lutein esters, phytosterol esters, vitamin A palmitate, vitamin C (ascorbyl palmitate), vitamin E (tocopherol), vitamin E acetate, vitamin K, vitamin A (palmitate), vitamin C (Palmitate), vitamin E blends, beta glucans, green tea, isoflavones, phytosterols, phytostanols, lutein, lycopene, and carotenoids. Most particularly suitable in the present invention is the dietary supplement coenzyme Q10 (Co-Q10).

Co-Q10 is a naturally occurring coenzyme conventionally used as a nutritional supplement and therapeutic agent. Chemically, Co-Q10 is 2,3-dimethoxy-5-methyl-6-decaprenyl-1,4-benzoquinone and is also known by the names ubiquinone, ubidecarenone, and Vitamin Q. It is classified as a fat soluble quinone. Co-Q10 is conventionally used as therapy for heart disease, cancer, immune depression, low energy and anti-wrinkling.

The bioavailability of these water-insoluble active agents is substantially limited for a variety of reasons. For example, the isoprenoid side chain of Co-Q10, results in a highly lipophilic molecule that is essentially insoluble in water and severely limits the oral bioavailability. The amount of active agent to be used is dependent upon the agent and the amount necessary to provide an effective amount to achieve the desired effect. For example, when using Co-Q10, a typical amount is that necessary to provide an antioxidating effect. Particularly suitable amounts are in the range of from about 0.1 to about 30%, more particularly about 5 to about 15%, by weight of the encapsulated formulation (active agent plus liposome plus starch).

The active agent, dissolved, if necessary, in a suitable solvent, is first incorporated into a liposome using methods well known in the art. In one such conventional method, lecithin is dissolved in water and homogenized under specific conditions. The lecithin stock solution is then mixed with an aqueous solution of selected surfactant(s). The liquid active ingredient is then added to the mixture, homogenized and microfluidized at very high shear to a particle size, typically, of less that 0.3 microns. The resulting liquid product is a stable lecithin-based liposome containing the active ingredient. The amount of liposome to be used is that necessary to effectively protect the active ingredient. Particularly suitable amounts are in the range of from about 0.5 to about 59.9%, more particularly about 10 to about 50%, by weight of the encapsulated formulation (active agent plus liposome plus starch).

The liquid liposome formulation is then encapsulated using a modified starch. Any starch or flour (hereinafter starch) is suitable as the base for the modified starch to be use herein and may be derived from any native source. A native starch, as used herein, is one as it is found in nature, including those developed by plant breeding, and bioengineered starches. Typical sources for the starches and flours are cereals, tubers, roots, legumes and fruits. The native source can be corn, pea, potato, sweet potato, banana, barley, wheat, rice, sago, amaranth, tapioca, arrowroot, canna, sorghum, oat and waxy or high amylose varieties thereof. As used herein, the term "waxy" or "low amylose" is intended to include a starch or flour containing at least about 95% by weight amylopectin and the term "high amylose" is intended to include a starch or flour containing at least about 40%, particularly at least about 70%, more particularly at least about 80%, amylose by weight. "Normal" as used herein, is intended to mean those starches which are not high or low amylose varieties. In particular, normal or low amylose varieties are particularly useful in the instant invention.

Also included as useful base starch materials are the conversion products derived from any of the above starches including fluidity or thin-boiling starches prepared by oxidation, α-amylase conversion, mild acid hydrolysis or heat dextrinization, and derivatized starch such as ethers and esters.

A particularly useful starch base is a gelatinized starch, that is a precooked, non-granular starch, and also may be a fluidity starch converted by mild acid degradation or heat dextrinization methods that are well known in the art. For example, see Rutenberg, "Starch and Its Modifications," *Handbook of Water-Soluble Gums and Resins*, Davidson, Editor, McGraw-Hill, Inc., New York, N.Y. 1980, pp. 22-36. A combination of one or more of these conversion techniques may be used. The conversion is typically carried out before treatment with a hydrophobic or a hydrophobic/hydrophilic reagent and before the enzyme treatment. If desired, the starch base may be converted by treatment with an α-amylase enzyme to produce a fluidity starch in the manner disclosed in U.S. Pat. No. 4,035,235. Where a high viscosity system is desired, it is not necessary to convert the base starch.

The starch may be derivatized by treatment with any reagent or combination of reagents which contributes encapsulation properties to the starch. The reagent must contain a hydrophobic moiety and may contain a hydrophilic moiety. The hydrophobic moiety should be an alkyl or alkenyl group which contains at least five carbon atoms, or an aralkyl or aralkenyl group which contains at least six carbon atoms, particularly up to about twenty-four carbon atoms. The hydrophilic moiety may be contributed by the reagent or the starch's own hydroxyl groups may serve as the hydrophilic moiety and the reagent may contribute only the hydrophobic moiety.

Any process for derivatizing starch which yields the desired blend of hydrophobic or hydrophobic and hydrophilic functions on the starch molecule and thereby yields stable encapsulation properties may be used to prepare the modified starch of the present invention. Suitable derivatives and methods for producing them are known in the art and disclosed in U.S. Pat. No. 4,626,288 which is incorporated herein by reference. In a particularly useful embodiment, the starch is derivatized by reaction with an alkenyl cyclic dicarboxylic acid anhydride by the method disclosed in U.S. Pat. Nos. 2,613,206 and 2,661,349, incorporated herein by reference, or propylene oxide, more particularly by reaction with octenylsuccinic anhydride.

Where a low viscosity is desirable, a particularly useful embodiment is an octenyl succinic half ester derivative of an amylopectin containing starch, such as waxy maize, which has been converted to a water fluidity (WF) of up to about 60. Water fluidity is an empirical test of viscosity measured on a scale of 0-90 wherein fluidity is the reciprocal of viscosity. Water fluidity of starches is typically measured using a Thomas Rotational Shear-type Viscometer (commercially available from Arthur A. Thomas Co., Philadelphia, Pa.), standardized at 30° C. with a standard oil having a viscosity of 24.73 cps, which oil requires 23.12±0.05 sec for 100 revolutions. Accurate and reproducible measurements of water fluidity are obtained by determining the time which elapses for 100 revolutions at different solids levels depending on the starch's degree of conversion: as conversion increases, the viscosity decreases. In a particularly useful embodiment, the converted starch is treated with from about 0.1% to about 3.0% for food products, and at least about 0.1% for other products, of octenyl succinic anhydride. In the alternative, a hydroxypropyl octenyl succinic derivative may be used.

For other products, any degree of substitution or level of conversion that results in the desired viscosity and encapsulation properties may be employed. For example, U.S. Pat. No. 4,035,235 disclosed a suitable embodiment comprising a method for producing a hydrophobic derivative of starch to be used as an alternative to gum arabic in encapsulating water insoluble substances, such as volatile flavoring oils and perfumes.

After derivatizing the starch, it is further enzymatically hydrolyzed by at least one enzyme capable of cleaving the 1,4-linkages of the starch molecule from the non-reducing ends to produce mono- and/or di-saccharides to provide high oxidation resistance, particularly those with less than about three glucose units, while maintaining substantially high molecular weight portions of the starch base to provide encapsulating properties. The enzymes useful in the present invention thus include, but are not limited to, β-amylase, glucoamylase, maltogenase, pullulanase, exo-alpha-1,4-glucosidase, exo-1,4-alpha-D-glucan maltotetrahydrolase, and exo-1,4-alpha-D glucan maltohexahydrolase, particularly β-amylase and glucoamylase.

The enzymatic hydrolysis of the starch base is carried out using techniques known in the art. The amount of enzyme used is dependent upon the enzyme, i.e., type, source and activity, and base material used as well as the amount of hydrolysis desired. Typically, the enzyme is used in an amount of from about 0.01 to about 1.0%, particularly from about 0.01 to 0.3%, by weight of the starch.

The optimum parameters for enzyme activity will vary depending upon the enzyme used. The rate of enzyme degradation depends upon factors known in the art, including the type of enzyme used, enzyme concentration, substrate concentration, pH, temperature, the presence or absence of inhibitors, and the degree and type of modification. These parameters may be adjusted to optimize the digestion rate of the starch base.

The starch may be gelatinized before enzyme hydrolysis. The gelatinization process unfolds the starch molecules from the granular structure, thereby permitting the enzyme to more easily and uniformly degrade the starch molecules.

Generally the enzyme treatment is carried out in an aqueous or buffered slurry at a starch solids level of about 10 to about 40%, depending upon the base starch being treated. A solids level of from about 15 to 35% is particularly useful, from about 18 to 25% more particularly useful, in the instant invention. In the alternative, the process may utilize an enzyme immobilized on a solid support.

Typically, enzyme digestion is carried out at the highest solids content feasible without reducing reaction rates in order to facilitate any desired subsequent drying of the starch composition. Reaction rates may be reduced by high solids content as agitation becomes difficult or ineffective and the starch dispersion becomes more difficult to handle.

The pH and temperature of the slurry should be adjusted to provide effective enzyme hydrolysis. These parameters are dependent upon the enzyme to be used and are known in the art. In general, a temperature of about 22 to about 65° C. is used, particularly from about 50 to about 62° C. In general, the pH is adjusted to about 3.5 to about 7.5, particularly from about 4.0 to about 6.0, using techniques known in the art.

The enzyme reaction is continued until a dextrose equivalent of at least about 20 and up to about 80, particularly about 20 to about 50, has been achieved, or until the desired end point (i.e., sufficient degradation to provide the desired functionality for the particular application) has been reached. The end point may be determined by a change in viscosity, by reducing sugar content (such as measured by dextrose equivalents), or by any other method known in the art for measuring the level of enzyme degradation of the starch molecule. In general, the enzyme reaction will take from about 0.1 to about 24 hours, particularly about 0.5 to about 4 hours. The time of the reaction is dependent upon the type of starch and enzyme used, the amount of enzyme used, and the reaction parameters of solids percent, pH, and temperature.

The enzyme degradation is then terminated by any technique known in the art such as acid or base deactivation, heat deactivation, ion exchange, and solvent extraction. For example, acid deactivation may be accomplished by adjusting the pH to lower than 2.0 for at least 30 minutes or heat deactivation may be accomplished by raising the temperature to about 85 to about 95° C. and maintaining it at that temperature for at least about 10 minutes to fully deactivate the enzyme. Heat deactivation is not suitable if a granular product is desired as the heat necessary to deactivate the enzyme will generally also gelatinize the starch.

The resultant solution is typically adjusted to the desired pH according to its intended end use. In general, the pH is adjusted to from about 5.0 to about 7.5, particularly from about 6.0 to about 7.0, using techniques known in the art. The modified starch may them be used to encapsulate the liposome emulsified active or dried for later use by methods known in the art, particularly spray drying. The modified starch may also be concentrated to remove much of the water before being used to encapusulate the liposome emulsified active.

The modified starch is characterized by a relatively low viscosity, moderately high dextrose equivalent, neutral taste, and by its unique functionality as an encapsulating agent.

The viscosity of the modified starch should be less than about 30 seconds, particularly from about 8 to about 25 seconds, more particularly from about 8 to about 15 seconds as measured by the funnel method. Viscosity is an important parameter in contributing to efficient encapsulation.

To measure the viscosity of the starch by the funnel method, the starch dispersion to be tested is adjusted to 19% or 25% (w/w) measured by refractometer. The temperature of the dispersion is controlled at 22° C. A total of 100 ml of the starch dispersion is measured into a graduated cylinder. It is then poured into a calibrated funnel while using a finger to close the orifice. A small amount is allowed to flow into the graduate to remove any trapped air and the balance is poured back into the funnel. The graduated cylinder is then inverted over the funnel so that the contents draw (flow) into the funnel while the sample is running. Using a timer, the time required for the 100 ml sample to flow through the apex of the funnel is recorded.

The glass portion of the funnel is a standard 58°, thick-wall, resistance glass funnel whose top diameter is about 9 to about 10 cm with the inside diameter of the stem being about 0.381 cm. The glass stem of the funnel is cut to an approximate length of 2.86 cm from the apex, carefully fire-polished, and refitted with a long stainless steel tip with is about 5.08 cm long with an outside diameter of about 0.9525 cm. The interior diameter of the steel tip is about 0.5952 cm at the upper end where is attached to the glass stem and about 0.4445 cm at the outflow end with the restriction in the width occurring at about 2.54 cm from the ends. The steel tip is attached to the glass funnel by means of a Teflon tube. The funnel is calibrated so as to allow 100 ml of water to go through in six seconds using the above procedure.

The modified starch should have a dextrose equivalent of at least about 20 and up to about 80. When glucoamylase is used to hydrolyze the derivatized starch, the DE is particularly from about 30 to about 50. When β-amylase is used, the DE is particularly from about 20 to about 50, more particularly from about 25 to about 38. Dextrose equivalent (DE) is defined as the reducing power of the hydrolyzate. Each starch molecule has one reducing end: therefore DE is inversely related to molecular weight. The DE of anhydrous D-glucose is defined as 100 and the DE of unhydrolyzed starch is virtually zero.

In the alternative, the derivatized starch may be blended with sugars, for example mono- di- or oligo-saccharides or maltodextrins, instead of producing the sugars in situ. The mono- di, and oligo-saccharides include all saccharides of up to about 10 glucose units, particularly those of up to about 3 glucose units, such as glucose, fructose, galactose, maltose, isomaltose, sucrose, lactose, raffinose, stachyose, fructosyl-sucrose, and maltooligosaccharides, particularly glucose, fructose, and maltose. The maltodextrins include those with a dextrose equivalent of from about 2 to about 50, particularly from about 5 to about 15.

The resultant starch/sugar blend should have a relatively high percent of sugars measured as glucose, at least about 20 and up to about 80%, particularly from about 40 to about 60%, sugar by weight.

The resultant starches (or starch/sugar blends), when used as encapsulating agents, have the advantages of achieving and maintaining consistently high load levels, low oil exposure, and excellent oxidation resistance.

The active agents may be encapsulated using the modified starches of the present invention and techniques known in the art, including but not limited to spray drying, extrusion, spray chilling, freeze-drying, and fluid bed coating. For example, the starch may be dispersed in water, the active agent may be added and emulsified, and the emulsion may then be spray dried to form the encapsulated product. The amount of starch to be used is that necessary to effectively encapsulate the active agent and liposome. Particularly suitable amounts are in the range of from about 30 to about 90%, more particularly about 30 to about 80%, by weight of the encapsulated formulation (active agent plus liposome plus starch).

When a starch/sugar blend is used, spray drying efficiencies may be decreased due to the high viscosity of the system and greater dryer deposits, particularly when mono-saccharides are used. Spray efficiencies may be increased by methods known in the art, such as using high drying towers, lightly oiling the chamber walls, or using preconditioned air in which the moisture has been substantially removed.

The encapsulated product prepared with the present encapsulating agents consistently achieve and maintain a relatively high load level of the specific active agent. Although load levels of the active agent plus liposome of greater than 40% may be realized, typically lower load levels based on the active agent alone are used. In particular, load levels of 0.1-25%, particularly 5-15%, of the active agent based on the entire formulation (wt/wt) are used. The level of active agent retained may be determined by methods known in the art such as by solvent extraction in the case of vitamins.

A high load level of active agent is desirable to reduce the cost of producing the final product as encapsulating agents are often expensive. Further, some encapsulating agents may contribute adverse or undesirable properties to the final system and it is thus desirable to reduce the amount of encapsulating agent used.

It is important not only to achieve a high load of active agent, but also to maintain it so as to enable a longer shelf life. Many active agents are volatile and/or labile. When the active agents are not encapsulated, they may be lost, producing undesirable variations in taste of the final products as perceived by the consumer. In addition, losses of such components increase the cost of the final products since it is necessary to increase the amount of the active to compensate for the losses which occur, and many are expensive.

In the case of an oil based active agent, the present encapsulating agents also retain the oil so as to provide a low surface oil. This is particularly true when glucoamylase is used to enzymatically hydrolyze the starch. The surface oil may be measured by methods known in the art such as by washing the encapsulated powder with a suitable solvent. Reduction of surface oil is important as increased surface oil indicates that the load of the active agent is not being maintained and inefficiency of encapsulation. Thus, reduction of surface oil results in a longer shelf life.

The present encapsulating agents also provide a relatively high level of oxidation resistance, thereby prolonging storage stability of the encapsulated product and shelf life of the final product. Oxidation resistance may be measured by methods known in the art. For example, oxidation resistance of encapsulating agents containing citrus oil may be determined by using gas chromatography (GC) to measure the amount of oxidization products of limonene, such as carvone, carviol, or limonene oxide, present in the oil extracted from powders aged at 50° C. for two weeks: less than about 0.8% carvone typically indicates acceptable levels of oxidation. Oxidation resistance is important not only for flavor considerations of the oil, but also to maintain the activity of various vitamins. To further increase oxidation resistance, an anti-oxidant may be added to the oil.

Most importantly, the active agent substantially retains its bioavailability. Encapsulation of active agents which have low bioavailability in the dry state, but not in the liquid state, is typically reduced to a great extent when encapsulated into a dry powder. This reduction of bioavailability necessitates the increase in active agent used in the final dosage form, which increases the cost of the dosage form significantly, particularly for the more expensive active agents. In particular, the active agent will be at least 50% bioavailable, more particularly at least 65% bioavailable.

The encapsulated product is effective when stored as a powder and spontaneously releases the active agent upon exposure to moisture. The resultant encapsulated product may be used at any level desired and may be added to food products or formed into a solid dosage form to be taken as a supplement. The encapsulated product may also be formulated into a personal care product or pharmaceutical for topical application. The amount used is dependent upon the amount of active agent to be incorporated and is often based upon a suggested daily intake for the vitamin or dietary supplement.

The encapsulated product can be used in various food products including, but not limited to, cereals; powdered drink mixes; instant coffees and teas; powdered sauce and gravy mixes; instant soups; cereals; powdered dressings; bakery products; flavors; fragrances; colorants; and other dry food products. Upon preparation of these powdered and instant products, the moisture triggers the release mechanism, providing the active agent to the consumer. In general, the encapsulated product will be used in an amount of from about 0.01 to about 10%, particularly from about 0.1 to about 5% by weight of the food product.

The encapsulated product may be used in a dietary supplement and ingested as a powder or in the form of a solid dosage form. In particular, the encapsulated product may be used in a solid tablet-like form (e.g. tablets and caplets) which may be ingested as such or effervesced (dissolved) prior to ingestion. The powdered encapsulate product may also be used in other forms known in the art, such as a powder-filled hard gelatin capsule. The encapsulated product may generally be used at the desired level, the amount being dependent upon the amount of active agent to be incorporated. In general, the encapsulated product will be used in an amount of from about 1 to about 95% by weight of the tablet.

The encapsulated product is particularly useful in a compressed tablet. The compressed tablet may be made using any method known in the art, particularly by direct compression of the tablet components. In the alternative, the tablet may be prepared by dry blending the encapsulated product with the other components of the formulation, granulating the mixture such as by fluid bed technology, roller compactor, extrusion, or high shear granulator, and dry compacting to a tablet.

Pharmaceutical excipients known in the art may be added to the pharmaceutical dosage form to impart satisfactory processing, compression, and disintegration characteristics to the formulation. Such excipients include, but are not limited to, diluents, flow enhancer, binders, lubricants and glidants, disintegrants, colors, flavors and sweetening agents. These excipients are well known in the art and are limited only by compatibility and characteristics desired.

Binders for the present invention include gelatin, microcrystalline cellulose, sugars, carboxymethyl cellulose, methyl cellulose, polyvinyl pyrrolidone, acacia, alginic acid, guar gum, hydroxypropyl methylcellulose, polyethylene oxide and ethyl cellulose.

Lubricants and glidants include talc, magnesium stearate, calcium stearate, stearic acid, glyceryl behenate, mineral oil, polyethylene glycol, sodium stearyl fumarate, stearic acid, vegetable oil, zinc stearate, and silicon dioxide.

Disintegrants suitable for the present invention include starches, algins, gums, croscarmelose, crospovidone, sodium starch glycolate, sodium laurel sulfate, microcrystalline cellulose, polacrilin potassium, and methylcellulose.

Diluents suitable for the present invention include dicalcium phosphate, calcium sulfate, lactose, cellulose, Kaolin, mannitol, sodium chloride, starch, sugars, calcium carbonate, calcium phosphate, dextrates, dextrin, dextrose, fructose, sorbitol, sucrose, and microcrystalline cellulose.

In particular, a binder is added to the tablet formulation to provide a tablet with the desired hardness. In general the hardness of the resultant tablet is at least about 3, more particularly at least about 4, most particularly at least about 6 kilopascals (kP).

If the final desired product is other than a pharmaceutical dosage form, alternative additives known to those arts may be present. For example, flavors and fragrances in a bath oil tablet to be used for topical application.

Upon contact with water, the moisture triggers the release mechanism, allowing the active agent to be released from the encapsulating starch. For example, upon digestion of the pharmaceutical dosage forms, the active agent is released to the body.

The following examples are presented to further illustrate and explain the present invention and should not be taken as limiting in any regard.

EXAMPLES

The following examples are presented to further illustrate and explain the present invention and should not be taken as limiting in any regard.
The following analytical tests were used to measure various parameters in the examples.
Determination of Dextrose Equivalents (DE)
The dextrose equivalent of starch may be determined by using the Reducing Sugars test described in Food Chemicals Codex, 4th ed., Jul. 1, 1996. Section 5, General Tests and Assays, Appendix X: Carbohydrates (Starches, Sugars, and Related Substances) or Standard Analytical Method #E-26 for Dextrose Equivalent from the Corn Refiners Association.
Determination of Percent Bioavailability by HPLC Analysis
Method of Analysis
Mobile Phase is Acetonitrile/2-Propanol/deionized water (68.75/28.75/2.50)
Column is Alltech Platinum EPS C 18 100A 5u
Flow Rate: 1 ml/min.
Injection Volume: 20 microlites (full loop)
Oven temperature: 33 C
Detector wavelength: 268 nm
Run Time: 7 min
Procedure
1) Plot calibration curve using standard samples containing 10, 25, 50, 75 and 100 ppm of CoQ10 using stock solution of 1000 ppm in Acetonitrile/2 Propanol (50/50).
2) Disperse 0.010 g of spray-dried CoQ10 powder into a vial containing 10.0 ml of deionized water. Transfer aliquots of the samples to injector vials and run chromatograph of the experimental samples to determine the CoQ10 levels.
3) Filter remaining experimental samples through a 0.45 micron cellulose acetate filter. Run chromatography of filtered experimental samples to determine the CoQ10 levels.
4) The amount of CoQ10 that passes through the 0.45 micron filter is a measure of the CoQ10 that is bioavailable Example 1

Preparation of the Derivatized Starch 500 grams of waxy maize starch were slurried in 750 ml water. The pH was adjusted to 7.5 using 3% sodium hydroxide. 15 grams of octenylsuccinic anhydride (OSA) were added in one-third increments every thirty minutes while maintaining the pH at 7.5 using 3% sodium hydroxide and constant agitation. The starch was then filtered out and washed with 750 ml water. The starch was then reslurried in 500 ml water and the pH adjusted to 5.5 with 3:1 hydrochloric acid. The starch was then filtered, washed with 750 ml water, and air dried to produce an OSA starch.

Example 2

Preparation of the Modified Starch a. Using Glucoamylase 100 grams of the OSA starch of Example 1 were slurried in 300 ml water and the pH adjusted to 5.5 using dilute hydrochloric acid. The slurry was gelatinized by jet cooking in a C1-339 jet cooker, commercially available from National Starch and Chemical Company, at 300° F., at a chamber pressure of 55 psi, and a slurry rate of 6 ml/min with the steam valve open at 75% capacity.

The temperature of the starch solution was then decreased to 55° C. 0.05% glucoamylase (AMG 200 L, commercially available from Novo Nordisk) based on the weight of the starch was added and the reaction was allowed to proceed at 55° C. with constant mixing for approximately 2.5 hours until a dextrose equivalent of 36 and a viscosity of 17 sec at 25% solids and 22° C. using the funnel method. The enzyme was then deactivated by heating the dispersion to 90° C. and maintaining the elevated temperature for 30 minutes. The dispersion was then cooled to room temperature and spray dried using an inlet temperature of 200° C., an outlet temperature of 100° C. and a feed rate of 65 ml/min.

b. Using β-Amylase 100 grams of the OSA starch of Example 1 were slurried in 300 ml water and the pH adjusted to 5.5 using dilute hydrochloric acid. The slurry was gelatinized by jet cooking in a C1-339 jet cooker, commercially available from National Starch and Chemical Company, at 300° F., at a chamber pressure of 55 psi, and a slurry rate of 6 ml/min with the steam valve open at 75% capacity.

The temperature of the starch solution was then decreased to 55° C. 0.2% β-amylase (Spezyme BBA 1500, commercially available from Genencor) based on the weight of the starch was added and the reaction was allowed to proceed at 55° C. with constant mixing for approximately 4 hours until a dextrose equivalent of 36 and a viscosity of 17 sec at 25% solids and 22° C. using the funnel method. The enzyme was then deactivated by heating the dispersion to 90° C. and maintaining the elevated temperature for 30 minutes. The dispersion was then cooled to room temperature and spray dried using an inlet temperature of 200° C., an outlet temperature of 100° C. and a feed rate of 65 ml/min.

c. Using a Combination of β-Amylase and Pullulanase 100 grams of the OSA starch of Example 1 were slurried in 300 ml water and the pH adjusted to 5.25 using dilute hydrochloric acid. The slurry was gelatinized by jet cooking in a C1-339 jet cooker, commercially available from National Starch and Chemical Company, at 290° F., at a chamber pressure of 40 psi, and a slurry rate of 3.5 ml/min with the steam valve open at 75% capacity.

The temperature of the starch solution was then decreased to 58° C. 5.0% of pullulanase (Promozyme, commercially available from Novo) by weight of starch was added and allowed to react for approximately 18 hours with constant mixing. Then 0.1% β-amylase (Spezyme BBA 1500, commercially available from Genencor) based on the weight of the starch was added and the reaction was allowed to proceed at 58° C. with constant mixing for approximately 2.5 hours until a dextrose equivalent of 32 and a viscosity of 14 sec at 25% solids and 22° C. using the funnel method. The enzymes were then deactivated by heating the dispersion to 95° C. and maintaining the elevated temperature for 30 minutes. The dispersion was then cooled to room temperature and spray dried using an inlet temperature of 200° C., an outlet temperature of 100° C. and a feed rate of 65 ml/min.

Example 3

Encapsulation of Liposomal Co-Q10

888 g. of the starch of Example 2b were dispersed in 2471 ml. Distilled water at 110° F. (43° C.) using mechanical agitation at moderate speed until no lumps were present. The starch solution was then slowly added to 1200 g. of the liposome/Co-Q10 mixture commercially available from 3i Corp. and maintained under moderate agitation for 10 minutes. The combined liquid mixture was spray dried in a Niro Utility Spray Dryer #3-068 using the centrifugal atomizer, an inlet temperature of about 302° F. (150° C.), and an outlet temperature of about 194° F. (90° C.) at a rate of about 100 ml/min.

The mean particle size (measured with the Horiba LA 900 particle size analyzer) of the Liposome/Co-Q10 mixture before mixing with starch was 0.120 microns. After the addition of starch, the particle size was 0.128 microns. The spray-dried powder contains 5.0% active CoQ10.

Example 4

Preparation of a Tablet

Tablets were prepared using the encapsulated product of Example 3, as follows. 600 g of the spray-dried powder containing 5% Co-Q10 were mixed with 387.5 g of anhydrous DT lactose commercially available from Sheffield Chemical Co., 5.0 g of magnesium stearate NF lubricant commercially available from Wico Corp., 5.0 g of Explotab (Sodium Starch Glycolate NF) disintegrant commercially available from Mendell Co. and 2.5 g of Cabo-Sil commercially available from Cabot Corp. 1000 mg tablets were prepared with a Piccola 10 station tablet press by subjecting the powder mixture to 3000 lbs compression force in a Piccola 10 station tablet press. Each tablet contains 30 mgs of Co-Q10 and has a crushing strength of 4-5 kP, as measured with a Pharmatron™ Model 6D tablet tester.

Example 5

Bioavailability of CoQ10 Encapsulated with Different Modified Starches

Liposomes of Co-Q10 were encapsulated using the method of Example 3, with different modified starches and component levels (percents), using the method described in example 3. bioavailability results are shown in Table I, below.

Starch 1 is a modified starch prepared according to Example 2b.

Starch 2 is a cold water soluble dextrin prepared by heating tapioca acidified to a pH of 3 by spraying small amounts of hydrochloric acid and heating from 72° F. (22° C.) to 200° F. (149° C.) for a period of five hours.

Starch 3 is a waxy corn starch hydrolyzed with hydrochloric acid and reacted with 3% octenyl succinic anhydride, then cooked at 30% solids by heating with steam at 250° f (121° C.) and spray dried to obtain a cold water soluble product.

TABLE I

| Starch | % starch | % liposome | % Co-Q10 | % bioavailability |
|---|---|---|---|---|
| Starch 1 | 48 | 42 | 10 | 66.7 |
| Starch 1 | 74 | 21 | 5 | 89.2 |
| Starch 2 | 48 | 42 | 10 | <1 |
| Starch 2 | 74 | 21 | 5 | <1 |
| Starch 3 | 48 | 42 | 10 | 22.7 |

Example 6

Preparation of Encapsulated Lycopene

Part A. Liposomal lycopene is prepared by dissolving 100 g of the antioxidant in 300 g of vegetable oil and adding the solution to a mixture of 200 g of lecithin and 1,200 mls of distilled water. The mixture is then homogenized and microfluidized at 20 PSI to obtain a final stable liposomal mixture containing 5.56% of lycopene, 11.11° A of lecithin, 16.67% of vegetable oil and 66.67% water.

Part B. 500 g of the modified starch prepared according to Example 2a are dissolved in 700 mls of distilled water and the solution slowly added to the liposomal lycopene and mixed for 30 minutes under moderate agitation. The Horiba particle size of the mixture is 0.2 microns before and after the addition of the modified starch. The liposomal mixture is then spray-dried according to the procedure described in example 3. The resulting spray-dried powder contains 9.1% stabilized lycopene Example 7

Preparation of a Derivatized Starch/Sugar Mixture a. 600 grams of an OSA derivatized starch prepared as in Example 1 were mixed with 400 grams glucose.

b. A cold water soluble, mildly acid degraded OSA starch was prepared by using the starch of Example 1, hydrolyzing using acid to a fluidity of about 60, and spray drying the starch. 600 grams of this starch were mixed with 400 grams glucose.

c. 500 grams of the starch prepared as in Example 6b were mixed with 500 grams maltose.

d. 340 grams of an OSA derivatized starch prepared as in Example 1 were mixed with 660 grams maltose.

e. 550 grams of an OSA derivatized starch prepared as in Example 1 were mixed with 450 grams glucose.

f. 500 grams of an OSA derivatized starch prepared as in Example 1 were mixed with 500 grams glucose.

g. 400 grams of an OSA derivatized starch prepared as in Example 1 were mixed with 600 grams glucose.

We claim:

1. A composition in the form of a dry powder comprising an aqueous insoluble active agent encapsulated in a plurality of liposomes, wherein said plurality of liposomes are further encapsulated in a matrix comprising:
   a gelatinized starch derivative, wherein the starch derivative is formed by reaction with an alkenyl cyclic dicarboxylic acid anhydride, and
   wherein the gelatinized starch derivative has been degraded by at least one enzyme capable of cleaving the 1,4-linkages of the starch molecule from the non-reducing ends to produce mono- or di-saccharides; and
   wherein at least 50% of the composition passes through a 0.45 micron cellulose acetate filter.

2. The composition of claim 1, wherein the starch is degraded to a dextrose equivalent of from about 20 to about 80.

3. The composition of claim 1, wherein the enzyme is selected from the group consisting of β-amylase, glucoamylase, pullulanase, maltogenase, exo-alpha-1,4-glucosidase, exo-1,4-alpha-D-glucan maltotetrahydrolase, and exo-1,4-alpha-D glucan maltohexahydrolase.

4. The composition of claim 1, wherein the starch is degraded to a dextrose equivalent of from about 20 to about 50 and the enzyme is β-amylase or glucoamylase.

5. The composition of claim 4, wherein the starch is degraded to a dextrose equivalent of from about 25 to about 38 and the enzyme is β-amylase.

6. The composition of claim 1, wherein the starch is gelatinized and has been derivatized by treatment with at least 0.1% of octenyl succinic acid anhydride on a starch dry weight basis.

7. The composition of claim 5, wherein the starch is gelatinized and has been derivatized by treatment with at least 0.1% of octenyl succinic acid anhydride on a starch dry weight basis.

8. The composition of claim 1, wherein the active agent is selected from the group consisting of coenzyme Q10, conjugated linoleic acid, omega 3/6 fatty acids (marine oils), saw palmetto, phophatidylcholine (PC), phophatidylserine (PS), lutein esters, phytosterol esters, vitamin A palmitate, vitamin C (ascorbyl palmitate), vitamin E (tocopherol), vitamin E acetate, vitamin K, vitamin A (palmitate), vitamin C (Palmitate), vitamin E blends, beta glucans, green tea, isoflavones, phytosterols, phytostanols, lutein, lycopene, and carotenoids.

9. The composition of claim 1, wherein the active agent is coenzyme Q10.

10. The composition of claim 6, wherein the active agent is coenzyme Q10.

11. The composition of claim 7, wherein the active agent is coenzyme Q10.

12. The composition of claim 1, wherein the starch is present in an amount of from about 30 to 90%, the active agent is present in an amount of about 0.1 to 30% and the liposomes are present in an amount of about 0.5 to 59.9% by weight.

13. The composition of claim 9, wherein the starch is present in an amount of from about 30 to 80%, the active agent is present in an amount of about 5.0 to 15% and the liposomes are present in an amount of about 10 to 50% by weight.

14. The composition of claim 1, wherein at least 65% of the composition passes through a 0.45 micron cellulose acetate filter.

15. A solid dosage form comprising the composition of claim 1.

16. A solid dosage form comprising the composition of claim 9.

17. A composition in the form of a dry powder, comprising:
an aqueous insoluble active agent encapsulated in a plurality of liposomes, wherein said liposomes are further encapsulated in a matrix comprising a gelatinized starch derivative,
wherein the starch derivative is formed by reaction with an alkenyl cyclic dicarboxylic acid anhydride, and,
at least one compound selected from the group consisting of a monosaccharide, a disaccharide, an oligosaccharide, and a maltodextrin;
and wherein at least 50% of the composition passes through a 0.45 micron cellulose acetate filter.

18. The composition of claim 17, wherein the starch is gelatinized and has been derivatized by treatment with at least 0.1% of octenyl succinic acid anhydride on a starch dry weight basis and the active agent is coenzyme Q10.

* * * * *